United States Patent
Pannu et al.

(10) Patent No.: US 11,801,381 B2
(45) Date of Patent: Oct. 31, 2023

(54) IMPLANTABLE NEUROMODULATION SYSTEM FOR CLOSED-LOOP STIMULATION AND RECORDING SIMULTANEOUSLY AT MULTIPLE BRAIN SETS

(71) Applicant: Lawrence Livermore National Security, LLC, Livermore, CA (US)

(72) Inventors: Satinderpall S. Pannu, Livermore, CA (US); Kedar G. Shah, Livermore, CA (US); Supin Chen, Livermore, CA (US); Marissa Crosetti, Livermore, CA (US); Timir B. Datta-Chaudhuri, Livermore, CA (US); Sarah H. Felix, Livermore, CA (US); Anna N. Ivanovskaya, Livermore, CA (US); Jason Jones, Livermore, CA (US); Kye Young Lee, Livermore, CA (US); Susant Patra, Livermore, CA (US); Vanessa Tolosa, Livermore, CA (US); Angela C. Tooker, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 163 days.

(21) Appl. No.: 15/764,553

(22) PCT Filed: Dec. 9, 2016

(86) PCT No.: PCT/US2016/065937
§ 371 (c)(1),
(2) Date: Mar. 29, 2018

(87) PCT Pub. No.: WO2017/100649
PCT Pub. Date: Jun. 15, 2017

(65) Prior Publication Data
US 2019/0054295 A1    Feb. 21, 2019

Related U.S. Application Data

(60) Provisional application No. 62/265,259, filed on Dec. 9, 2015.

(51) Int. Cl.
*A61N 1/36* (2006.01)
*A61N 1/05* (2006.01)
(Continued)

(52) U.S. Cl.
CPC ............. *A61N 1/0531* (2013.01); *A61N 1/04* (2013.01); *A61N 1/05* (2013.01); *A61N 1/0534* (2013.01);
(Continued)

(58) Field of Classification Search
CPC ..................... A61N 1/36139; A61N 1/37514
See application file for complete search history.

(56) References Cited

U.S. PATENT DOCUMENTS

| | | | |
|---|---|---|---|
| 6,230,049 | B1 | 5/2001 | Fischell et al. |
| 6,480,743 | B1 | 11/2002 | Kirkpatrick et al. |

(Continued)

FOREIGN PATENT DOCUMENTS

| | | |
|---|---|---|
| WO | WO-2014190167 A2 | 11/2014 |
| WO | WO-2016201151 A1 | 12/2016 |

OTHER PUBLICATIONS

International Search Report and Written Opinion issued in PCT/US2016/065937, dated Apr. 7, 2017; ISA/KR.

*Primary Examiner* — Rex R Holmes
*Assistant Examiner* — Jennifer L Ghand
(74) *Attorney, Agent, or Firm* — HARNESS, DICKEY & PIERCE, P.L.C.

(57) ABSTRACT

The present disclosure relates to a modular system for deep brain stimulation (DBS) and electrocorticography (ECoG). The system may have an implantable neuromodulator for generating electrical stimulation signals adapted to be applied to a desired region of a brain via an attached electrode array. An aggregator module may be used for collecting and aggregating electrical signals and transmit- (Continued)

ting the electrical signals to the neuromodulator. A control module may be used which is in communication with the aggregator module for controlling generation of the electrical signals and transmitting the electrical signals to the aggregator.

16 Claims, 4 Drawing Sheets

(51) Int. Cl.
    *A61N 1/04*     (2006.01)
    *A61N 1/375*     (2006.01)
    *A61N 1/372*     (2006.01)
    *A61N 1/378*     (2006.01)
    *A61B 5/00*     (2006.01)
    *A61B 5/291*     (2021.01)

(52) U.S. Cl.
    CPC ....... *A61N 1/36139* (2013.01); *A61N 1/3787* (2013.01); *A61N 1/37217* (2013.01); *A61N 1/37247* (2013.01); *A61N 1/37514* (2017.08); *A61B 5/291* (2021.01); *A61B 5/4836* (2013.01); *A61N 1/36067* (2013.01); *A61N 1/375* (2013.01)

(56) References Cited

U.S. PATENT DOCUMENTS

| | | | |
|---|---|---|---|
| 6,597,954 B1* | 7/2003 | Pless | A61B 5/0476 600/544 |
| 10,960,215 B2* | 3/2021 | Reed | A61N 1/37229 |
| 2004/0088027 A1* | 5/2004 | Burnes | G16H 10/60 607/60 |
| 2006/0058627 A1 | 3/2006 | Flaherty et al. | |
| 2006/0149339 A1* | 7/2006 | Burnes | G16H 10/60 607/60 |
| 2009/0270948 A1* | 10/2009 | Nghiem | A61B 5/0031 607/60 |
| 2009/0292336 A1 | 11/2009 | Nishida et al. | |
| 2010/0082302 A1* | 4/2010 | Garudadri | A61B 5/0006 702/189 |
| 2010/0164688 A1* | 7/2010 | Chakraborty | H02J 50/50 340/10.1 |
| 2010/0179615 A1* | 7/2010 | Zhang | H01L 41/25 607/57 |
| 2011/0009927 A1* | 1/2011 | Parker | A61N 1/3605 607/62 |
| 2014/0277257 A1 | 9/2014 | Perryman et al. | |
| 2015/0157862 A1* | 6/2015 | Greenberg | H05K 1/11 607/60 |
| 2016/0243363 A1* | 8/2016 | Meskens | A61N 1/37252 |

* cited by examiner

IMPLANTABLE NEUROMODULATION SYSTEM FOR CLOSED-LOOP STIMULATION AND RECORDING SIMULTANEOUSLY AT MULTIPLE BRAIN SETS

CROSS-REFERENCE TO RELATED APPLICATIONS

This application is a 371 National Phase of PCT/US2016/065937 filed Dec. 9, 2016 and published in English as WO 2017/100649 A1 on Jun. 15, 2017, which claims the benefit of U.S. Provisional Application No. 62/265,259, filed on Dec. 9, 2015. The entire disclosure of the above applications are incorporated herein by reference.

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to systems and methods for Deep Brain Stimulation and electrocorticography arrays, and more particularly to a system and method for performing closed loop neuromodulation and stimulation on a plurality of areas of a brain simultaneously.

BACKGROUND

This section provides background information related to the present disclosure which is not necessarily prior art.

Deep brain stimulation ("DBS") is an established treatment for movement disorders such as Parkinson's disease, essential tremor, and dystonia. Although there are many on-going investigations into other potential uses of DBS, such as psychiatry, studies have been limited by available technology due to large electrode size, a low number of simultaneous recording and stimulation sites, and component size restrictions on anatomical target sites.

Multiple target sites are especially important for studying and treating the brain as a "network" because multiple regions can be associated with a neural disorder. An example is Parkinson's disease where therapeutic effects from deep brain stimulation can be confirmed with recordings from the brain surface from electrocorticography ("ECoG").

Another potential example where DBS can be therapeutic is in treating depression. Depression is often associated with several brain regions such as the ventral capsule/ventral, striatum, Brodmann area 25, nucleus accumbens, lateral habenula, and medial forebrain bundle. However, previous clinical trials for treating depression (e.g., Medtronic RECLAIM study, St. Jude BROADEN study) failed to show a significant difference in response rates between the DBS administered group and the control group.

Commercially available systems for simultaneous recording and stimulation of the brain, such as the Medtronic Activa PC+S and NeuroPace RNS, are not capable of more than two target sites. Furthermore, they also only have four to eight channels per target site which restricts high resolution spatial coverage. To improve understanding and treatment, new technologies with the ability to record and stimulate simultaneously from a greater number of channels from multiple regions of the brain are required.

SUMMARY

This section provides a general summary of the disclosure, and is not a comprehensive disclosure of its full scope or all of its features.

In one aspect the present disclosure relates to a modular system for deep brain stimulation (DBS) and electrocorticography. The system may comprise an implantable neuromodulator for generating electrical stimulation signals adapted to be applied to a desired region of a brain via an electrically coupled electrode array. An aggregator module may be included for collecting and aggregating electrical signals and transmitting the electrical signals to the neuromodulator. A control module may be included which is in communication with the aggregator module for controlling generation of the electrical signals and transmitting the electrical signals to the aggregator.

In another aspect the present disclosure relates to a modular system for deep brain stimulation (DBS) and electrocorticography. The system may comprise an implantable neuromodulator array for applying electrical stimulation signals to a desired region of a brain via an electrically coupled electrode array, and for transmitting electrical signals representing brain activity. An aggregator module may be included for collecting and aggregating electrical signals and transmitting the electrical signals to the neuromodulator, and for receiving the electrical signals representing brain activity and recording information representing the brain activity. A control module may be included in communication with the aggregator module for controlling generation of the electrical signals and transmitting the electrical signals to the aggregator, and for receiving the information representing brain activity.

In still another aspect the present disclosure provides a method for deep brain stimulation (DBS) and electrocorticography. The method may comprise using a neuromodulator adapted to be implanted in a brain, and configured to generate electrical stimulation signals adapted to be applied to a desired region of the brain via an electrically coupled electrode array. An aggregator module may be used to communicate with the neuromodulator and to collect and aggregate electrical signals, and to transmit the electrical signals to the neuromodulator for use by the neuromodulator in generating the electrical stimulation signals. A control module may be used which is configured to be carried on a person, to communicate with the aggregator module and to generate the electrical signals used by the aggregator module.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present disclosure is directed to a system and method which provides closed-loop neuromodulation across multiple brain sites. The system of the present disclosure makes this possible in part by using low profile implantation packages, together with high-density interconnections and direct integration of bare die. The system provides the additional significant benefit of being both modular and scalable. This enables the system to be easily configured for use with a selected number of implants at a selected number of locations, and using a selected number of channels. This significant flexibility enables personalized treatment and easy access to many physically distinct brain regions. The architecture of the system also reduces the amount of electrical conductors required for providing power and data transfer between various electronic components and the sensors at various sites of the brain. The electronics provided by the system allows for processing and storage of data, as well as autonomous closed-loop operation. Data obtained by the system is available for real time processing.

Figure 1:
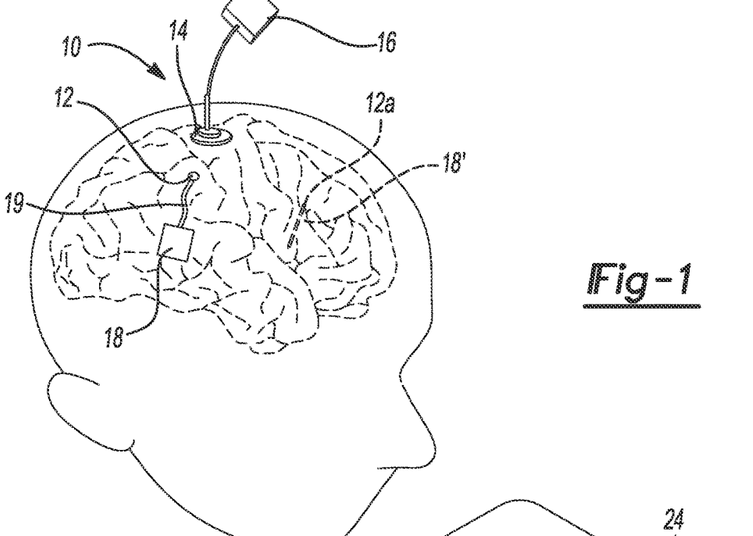
FIG. 1 is a high level illustration of one embodiment of a system in accordance with the present invention being used on a human brain.

Referring to FIG. 1, a high level diagram of one embodiment of a system 10 in accordance with the present disclosure is illustrated. The system 10 in this embodiment may include a first neuromodulator 12, a second neuromodulator 12a, an aggregator module 14 and a control module 16. The neuromodulator 12 may be implanted in the brain along with another electrical connection device in the form of an electrode array 18 which is electrically and mechanically coupled to the neuromodulator 12 through an electrical connection assembly 20' (not shown) and an electrically conductive cable 19. One example of the electrode array 18 is provided in co-pending PCT application PCT/US16/36775 filed on Jun. 9, 2016, the entire disclosure of which is hereby incorporated by reference into the present disclosure. It will be appreciated then that the electrode array 18 and the electrical connection assembly 20' may both be termed "electrical connection devices."

The neuromodulator 12a, which in this example is connected to a cylindrical electrode array 18', is especially well adapted for DBS. Neuromodulator 12 in this example is connected to a planar electrode array which is especially well adapted for electrocorticography ("ECoG"). Neuromodulator 12 provides a highly compact, implantable package for providing DBS or ECoG stimulation and is shown in FIG. 1 implanted within a human brain. The aggregator module 14 may be in bidirectional communication with the neuromodulator 12a and the control module 16. The aggregator module 14 operates to route and distribute data and control information between the neuromodulator 12a and the control module 16. While the following discussion will focus on the system 10 having one neuromodulator 12 connected to the planar electrode array 18, it will be appreciated that in many applications two or more neuromodulators 12 and/or 12a and their attached electrode arrays will be included, and implementations which include different numbers and combinations of the neuromodulators 12 and/or 12a, using the teachings presented herein, are anticipated. Thus, the system 10 is not limited to only one configuration for the neuromodulator(s) 12 employed.

Figure 2:
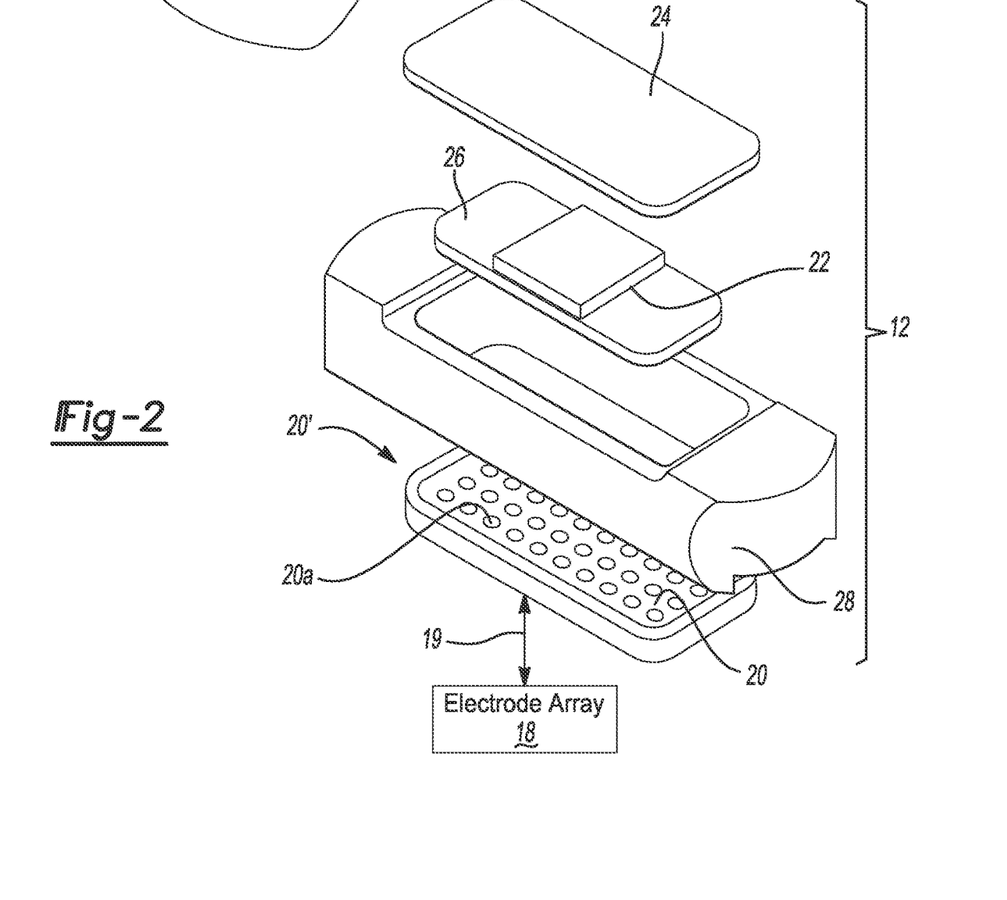
FIG. 2 is a high level exploded perspective illustration of a plurality of components which may be used to form one embodiment of the neuromodulator shown in FIG. 1, and where the neuromodulator is electrically coupled to a remotely located electrode array via an electrical connection assembly.

Referring to FIG. 2, the neuromodulator 12 is shown in greater detail. The neuromodulator 12 forms a highly compact electronics package for recording electrical signals and for providing electrical stimulation signals for DBS purposes. The neuromodulator 12, in one embodiment, may form a 64 channel device that is connected to the electrode array 18 through electrical cable 19 and through the electrical connection assembly 20'. The electrical connection assembly 20' of the neuromodulator 12 may have a ceramic portion 20 (shown simply in diagrammatic form) populated with a plurality of electrical feedthroughs 20a which are in communication with a corresponding plurality of conductive bond pads 20b. The neuromodulator 12 may also include a multiplexer chip 22, a lid 24 (e.g., plastic), an interposer 26, and a housing 28 for encapsulating the electrical connection assembly 20', the multiplexer chip 22 and the interposer 26. Although the exact number of bond pads 20b and electrical feedthroughs 20a used to form the electrical connection assembly 20' may vary widely to meet specific applications, in one example the electrical connection assembly 20' may have 32 to 40 independent bond pads 20b, but as noted above greater or lesser quantifies of bond pads may be used. Each electrode of the electrode array 18 may also range widely in size to suit a specific application and to meet the needs for stimulation of neural tissue and/or recording of electrical signals generated within neural tissue. Some electrode arrays 18 may also have a counter electrode which forms a return current path for a stimulating current being applied to the neural tissue, and a reference electrode for differential recording. Both cylindrical electrode arrays for DBS and planar arrays for ECoG may be used to cover a full range of brain regions.

Figures 3, 4:
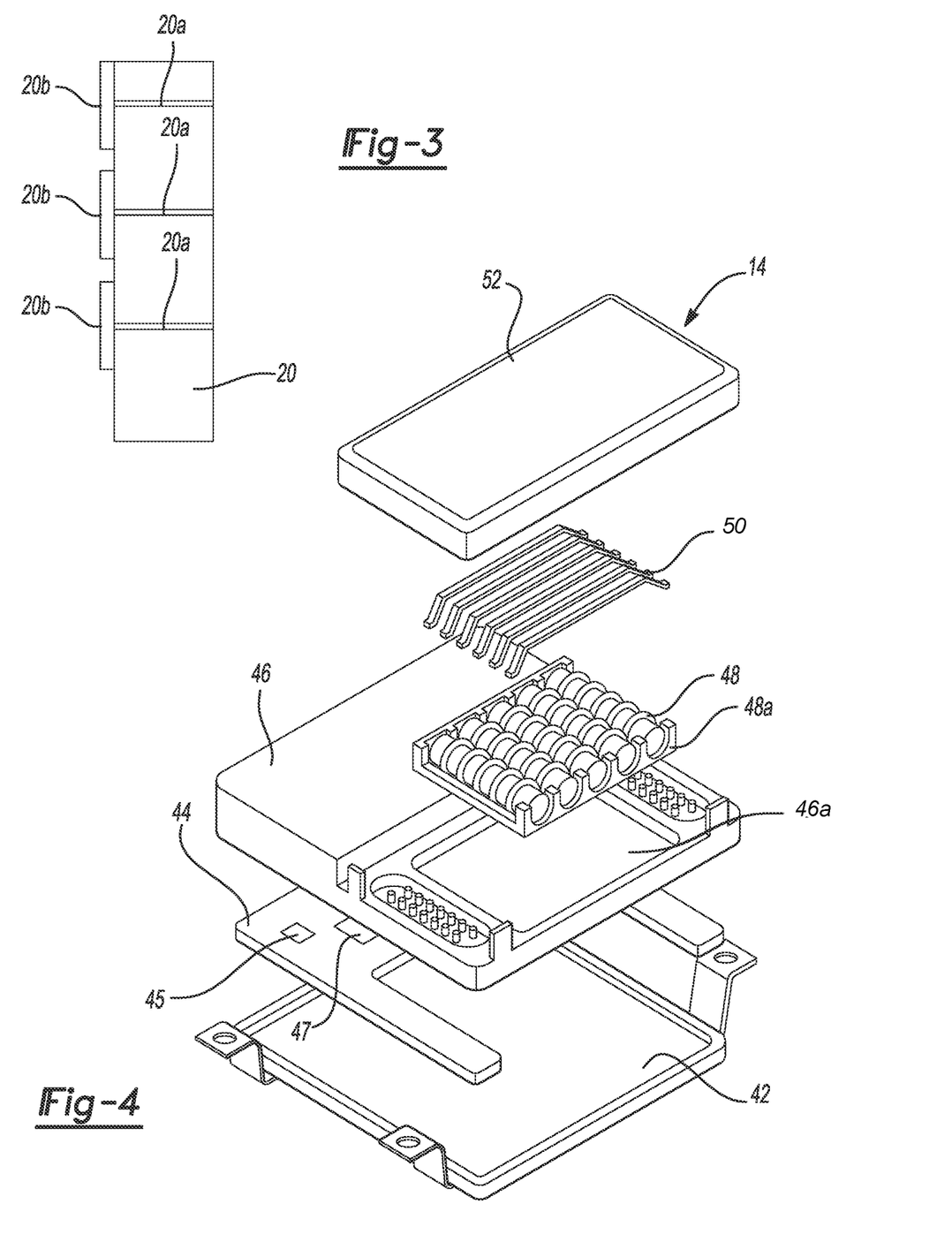
FIG. 3 is a simplified side cross sectional view of the ceramic component of the neuromodulator of FIG. 2, further illustrating the conductive feedthroughs and electrically connected bond pads that enable electrical attachment to the individual electrodes of the electrode array.
FIG. 4 shows an exploded perspective view of the aggregator module and its various components and subsystems.

With specific reference to FIG. 3, the ceramic portion 20 of the neuromodulator 12 is shown in highly simplified form. The ceramic portion 20 may be manufactured with the electrical feedthroughs 20a that terminate on the conductive bond pads 20b. In this example the bond pads 20b form electrical contact or connection points that can be electrically connected to the individual electrodes of an electrode array (not shown) through electrical traces in a connection cable, such as cable 19 in FIGS. 1 and 2.

The neuromodulators 12 and 12a each form compact electronics packages having embedded electronics for simultaneous low-noise recording and stimulation. The neuromodulators 12 and 12a may each also monitor electrode impedance to ensure system reliability and stimulation safety, and check that electrical stimulation pulses are within compliance (e.g., with predetermined voltage and/or current ranges). The entire neuromodulator 12 and/or 12a may be formed with a form factor that is less than about 5 mm×8 mm×3 mm for chronic subcutaneous implantation.

Figure 5:
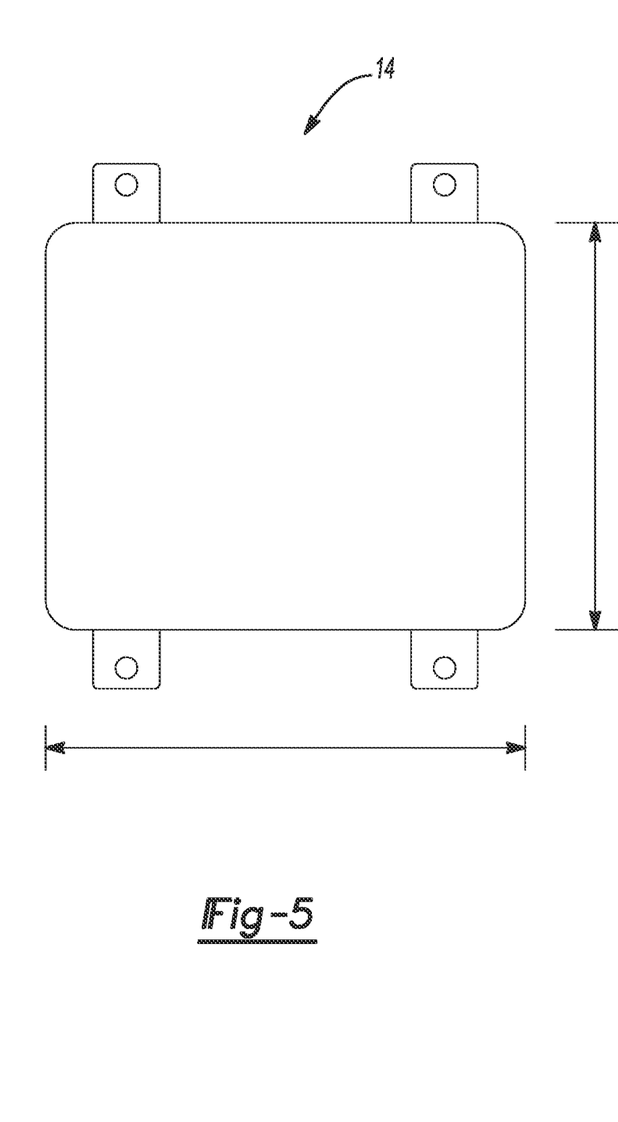
FIG. 5 shows a plane view of the assembled aggregator module with dimensions which give one example of the form factor of the aggregator module.
Figure 6:
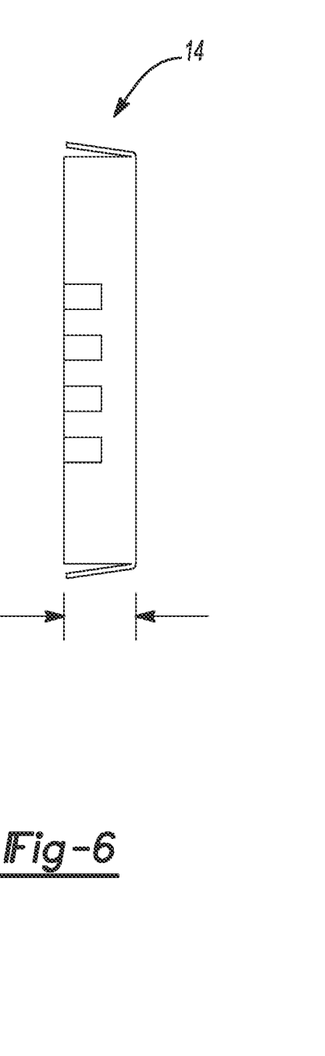
FIG. 6 is a side view of the assembled aggregator module further illustrating one example of the form factor thereof.

Referring to FIGS. 4-6, one embodiment of the aggregator module 14 is shown. The aggregator module 14 routes and distributes electrical signals in the form of data and control information between one or more neuromodulators 12 and/or 12a and the control module 16. The aggregator module 14 may also receive electrical signals from the neuromodulators 12 and/or 12a, which represent real time brain wave activity, if the neuromodulator 12 or 12a is/are configured to obtain such signals. The aggregator module 14 also distributes power to each neuromodulator 12 and/or 12a and enables a flexible connection of varying numbers of neuromodulators 12 and/or 12a to the single control module 16. In one embodiment data and power may be transmitted between the aggregator module 14 and the control module 16, and/or to and from the neuromodulator 12 and/or 12a, with a 6-wire interface (for example, cradle 48a illustrates five slots with implantable electrical connections 48 representing a 6-wire interface). The aggregator module 14 may be a component which is carried on the person of an individual or it may be mounted in the skull of an individual, or possibly implanted at other locations on the individual's body. The aggregator module 14 may use the SYGNUS• implantable contact system and it may be laser welded to provide for hermetic sealing.

In the example shown in FIGS. 4-6, the aggregator module 14 includes a lid 42, a printed circuit board (PCB) 44 having a short range wireless transceiver 45 and an on-board microprocessor 47, a housing 46 having a recess 46a, an implantable electrical connections component 48 configured to fit within the recess 46a, a jumper 50 and an overmold 52. The jumper 50 forms a protected connection to the neuromodulator 12 (or 12a) and control module 16 so that quick modifications to circuit connections can be effected. The implantable electrical connections of the component 48 are made from only biocompatible materials which helps to ensure that body materials do not damage any portion of the aggregator module 14. The assembled aggregator module 14, in one preferred embodiment, may have a length of about 30-35 mm, a width of about 30 mm and a thickness of about 4-5 mm, although it will be appreciated that these dimensions may vary considerably to suit specific applications.

Figure 7:
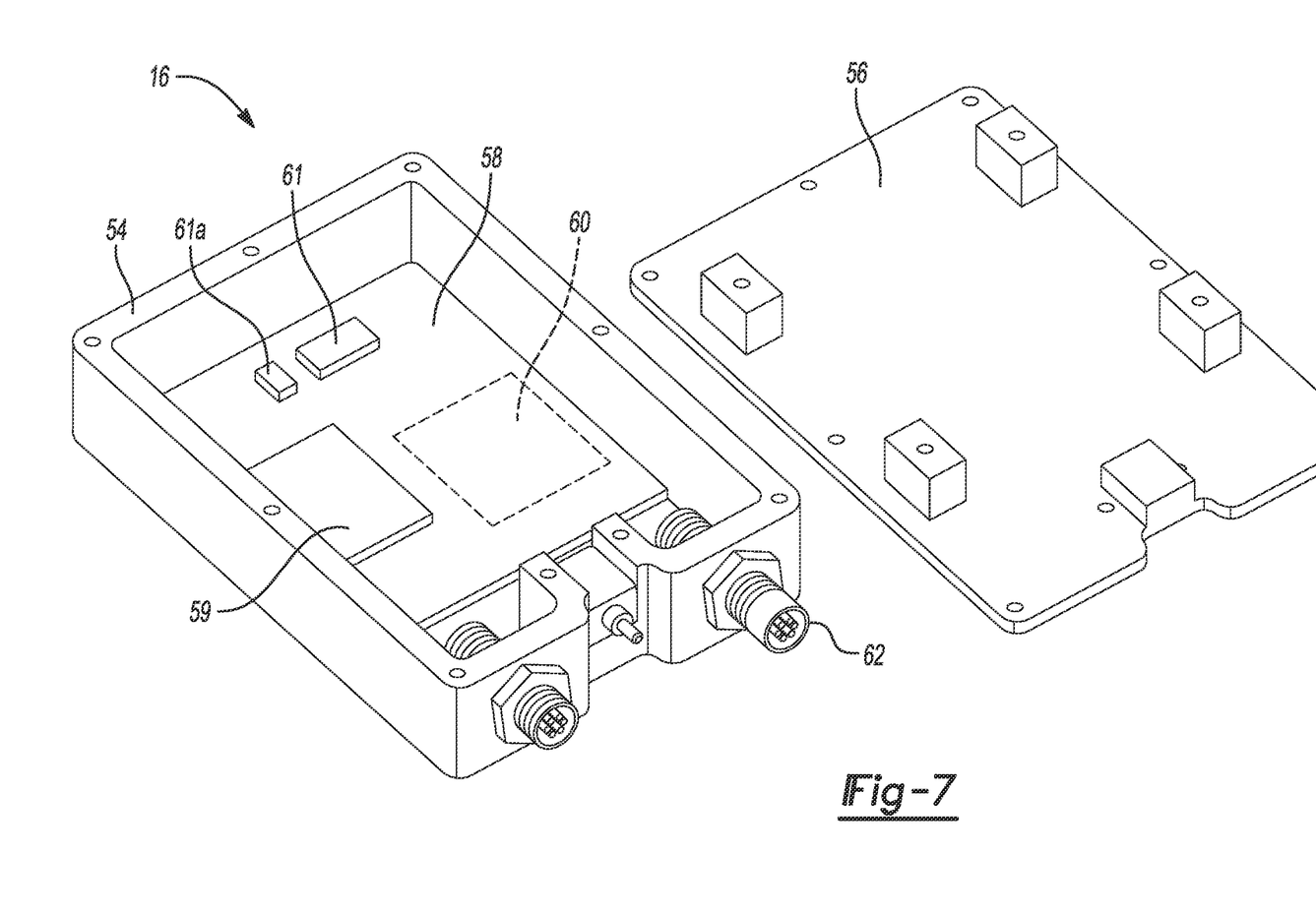
FIG. 7 is a high level perspective view of the control module.

Referring to FIG. 7, a high level perspective view of one embodiment of the control module 16 is shown. In this example the control module 16 includes a housing 54, a lid 56, a printed circuit board 58 having its own on-board microprocessor 59 and a short range, wireless transceiver 61, and memory 61a, which are all adapted to on the PCB 58 within the housing. An on-board battery 60, which in one implementation is positioned below the PCB 58, and therefore indicated by dashed lines in FIG. 7, may be included for powering the electrical components on the PCB 58 and providing electrical stimulation signals to the electrode array 18. The battery 60 may be a rechargeable battery or it may be a non-rechargeable battery. An Input/Output interface component 62 may also be included that enables electrical coupling to the aggregator module 14. The control module 16 may communicate wirelessly with both an external device (e.g., smartphone, laptop, desktop, tablet, etc.) and with the aggregator module 14, via its wireless transceiver 61.

The control module 16 handles computation and command generation, data acquisition and storage, and power management to enable the system 10 to run independently over extended periods of time. The control module 16 also supports advanced data processing of recorded signals for closed-loop control of stimulation rate, amplitude and timing. Power is stored in the battery 60 and the battery can be replaced or wirelessly recharged. The module 16 also can communicate data wirelessly with an external electronic device (e.g., personal digital assistant, laptop, desktop computer, tablet, smartphone, etc.). The control module 16 can be in the form of an external module which is carried on the person, such as on a belt, or even implanted in the chest. The housing 54 is preferably made of plastic, and is therefore transparent to RF signals and chemically resistant to fluids, humidity, sweat, etc. The control module 16 receives the aggregated data stream from the aggregator module 14, which is the data stream combined from the electrode array 18 of the neuromodulator 12. The neural recordings may then be processed by one or more algorithms stored in memory associated with the on-board microprocessor 59 of the control module 16, and the appropriate stimulation patterns are determined by the microprocessor and then communicated to the aggregator module 14. These signals may be sent wirelessly by the control module 16 using its short range wireless transceiver 61 or they may be sent via a wired connection with the aggregator module 14. The signals are used by the electrode array 18 of the neuromodulator 12 to apply the appropriate neural stimulation. The wireless transceiver 61 of the control module 16 also enables a wireless link to an external device for data transfer that allows custom algorithms to be uploaded to the microprocessor 59 of the control module 16, as well as the wireless downloading of recorded data.

The system 10 provides both high spatial density cortical and subcortical electrode arrays with embedded electronics which enables simultaneous recording and stimulation from multiple sites on both hemispheres of the brain. The system 10 further provides for flexible and modular data aggregation to integrate and control the data stream from the neural interfaces, and includes sufficient computation, storage and energy to enable the system to run independently over extended periods without recharging by the control module 16. This novel platform will enable clinicians to develop and implement real-time, closed-loop neuromodulation based on neural stimuli with temporal and spatial resolution not possible before.

The cylindrical electrode array associated with neuromodulator 12a may be surgically implanted via stereotactic placement. The system 10 enables recording from both hemispheres and multiple cortical areas. Each neuromodulator 12 and/or 12a has the capability to record and stimulate from each electrode included in the array. The modular approach of the system 10, together with wireless communications between the neuromodulator 12 (and/or the neuromodulator 12a) and the aggregator module 14, enables the neurosurgeon to flexibly select brain areas for implantation depending on the individual targets for each neuropsychiatric disorder without the constraints of tethered wires.

The aggregator module 14, with its embedded processor, enables the deployment of closed-loop algorithms which can be wirelessly reprogrammed. This technology enables the capability to "read-out" spatiotemporal patterns of neural activity in each recording area of the brain, across multiple areas simultaneously, and conversely, to "read-in" information to neural targets by patterned electrical stimulation. The system 10 introduces a highly-scalable approach, allowing for simultaneous stimulation and recording from large numbers of channels in multiple cortical and subcortical areas. The combination of modularity and the highly-miniaturized electronics eliminates the complicated interconnects, thus enabling a practical and translatable method of interfacing simultaneously with many cortical regions. This represents a significant technical advance over current neural stimulation systems with their highly constrained and fixed stimulation settings. The system 10 is expected to to enable innovative treatment strategies for guiding rehabilitative neural plasticity.

Still another benefit of the system 10 is that it is reconfigurable based on the specific neuropsychiatric disorder and the patient-specific therapy. The low-power, integrated circuit technology employed by the various modules of the system 10, combined with the modularity of the system and wireless communications capability, ensures that the system can be adapted, reconfigured as needed (e.g., software updates), and contains sufficient computational power to process information in real time.

The present system and method is expected to find utility in a wide variety of current studies and treatments involving DBS such as with movement disorders (e.g., Parkinson's Disease, dystonia, essential tremors), epilepsy, neuropsychiatric disorders (e.g., addiction, major depression, chronic pain, etc.), and obsessive compulsive disorder (OCD). The system 10 has the potential to improve neuromodulation for diagnostics and therapeutics by enabling closed-loop stimulation based on sensing from multiple brain sites, which is an important function when most relevant stimulation and recording sites are within different brain regions. The system 10 also enables the study of brain plasticity (altering physiology and anatomy over time) as a response to DBS.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular system for deep brain stimulation (DBS) and electrocorticography, comprising:
   an implantable neuromodulator configured to generate first electrical signals representing electrical stimulation signals adapted to be applied to a desired region of a brain via an electrically coupled electrode array;
   an aggregator module configured to be at least one of:
      carried on a person; or
      implanted in a bodypart of the person;
   the aggregator module having a housing and including an embedded processor and the housing including a portion for supporting an implantable electrical connections component in an independent compartment area of the housing sealed via an overmold component affixed to the housing, the independent compartment having a recess configured to hold the implantable electrical connections component therein such that the overmold component covers the recess without impeding access to the embedded processor, the implantable electrical connections component configured to receive second electrical signals from the implantable neuromodulator, for transmitting third electrical signals to the implantable neuromodulator, and for distributing power to the implantable neuromodulator;
   a control module in communication with the aggregator module and including a microprocessor, a memory, at least one algorithm stored in the memory for determining neural stimulation patterns, and an on-board battery, the control module configured to control the aggregator module to generate the third electrical signals, or to aggregate the second electrical signals as the second electrical signals are received from the implantable neuromodulator for subsequent transmission to the control module; and
   the aggregator module forming an independent component able to be supported on a human body at a different location from the implantable neuromodulator, and further enabling communication of power and data signals between the control module and the aggregator module; and
   the control module further configured to:
   use the microprocessor and the at least one algorithm to determine and generate the neural stimulation patterns, based on the electrical signals received from the aggregator module, and to generate and communicate the neural stimulation patterns back to the aggregator module for distribution by the aggregator module as the third signals to the implantable neuromodulator.

2. The system of claim 1, wherein the implantable neuromodulator is connected to the electrode array via an electrical cable, and wherein the electrode array forms a planar configuration electrode array.

3. The system of claim 1, wherein the implantable neuromodulator is connected to the electrode array via an electrical cable, and wherein the electrode array comprises a cylindrical configuration electrode array.

4. The system of claim 1, wherein the implantable neuromodulator includes a multiplexer for distributing electrical signals to and from various units of the electrodes.

5. The system of claim 1, wherein the aggregator module includes a wireless transceiver for wirelessly communicating with the control module.

6. The system of claim 1, wherein the control module includes a wireless transceiver for communicating wirelessly with the aggregator module.

7. The system of claim 1, wherein the implantable neuromodulator is configured to provide the second electrical signals back to the aggregator module.

8. The system of claim 7, wherein the memory of the control module is configured to store data related to the second electrical signals received by the aggregator module.

9. The system of claim 1, wherein the control module includes an interface.

10. The system of claim 1, wherein the on-board battery is rechargeable.

11. The system of claim 1, wherein the implantable neuromodulator forms a hermetically sealed component.

12. The system of claim 1, wherein the aggregator module forms a hermetically sealed component.

13. A modular system for deep brain stimulation (DBS) and electrocorticography, comprising:
   at least one implantable neuromodulator array configured to communicate with an electrode array having a plurality of electrically coupled electrodes, to apply first electrical stimulation signals to a desired region of a brain, and for transmitting neural electrical signals representing brain activity;
   an aggregator module including an embedded processor and an electrical connections component having a plurality of implantable electrical connections, the aggregator module configured to be implanted within a bodypart of a person as an independent module, and the aggregator module configured for collecting and aggregating the neural electrical signals and transmitting electrical control signals to the implantable neuromodulator array, and for recording information representing the brain activity determined from the neural electrical signals, and for distributing power to the implantable neuromodulator array;

a control module including a processor, a memory for storing one or more algorithms, and an on-board battery, the control module being in communication with the aggregator module for controlling generation of the electrical control signals and transmitting the electrical control signals to the aggregator module, and for receiving the neural electrical signals representing brain activity from the aggregator module; and wherein the aggregator module enables data and power signals to be transmitted between the control module and the aggregator module, and wherein the aggregator module includes:
- a housing having a recess formed on one surface, the recess being configured to receive the electrical connections component;
- a wireless transceiver for wirelessly communicating with the control module; and
- an overmold configured to be secured to the housing and to cover the electrical connections component without impeding access to the embedded processor; and wherein the control module is further configured to:
use the processor and the one or more algorithms to determine appropriate neural stimulation patterns, based on the neural electrical signals received from the aggregator module, and to communicate the appropriate neural stimulation patterns back to the aggregator module for distribution to the at least one implantable neuromodulator array.

14. The system of claim 13, wherein the control module includes a memory for storing data related to the neural electrical signals received by the aggregator module.

15. A method for performing deep brain stimulation (DBS) and electrocorticography, comprising:
using a neuromodulator adapted to be implanted in a brain, and configured to generate first electrical signals forming electrical stimulation signals adapted to be applied to a desired region of the brain via an electrically coupled electrode array;

using an aggregator module forming an independent component able to be supported apart from the neuromodulator, and having an electrical connections component having a plurality of implantable electrical connections, and being configured to be carried on a person to:
communicate with the neuromodulator;
collect and aggregate second electrical signals received from the neuromodulator representative of neural signals;
transmit third electrical signals to the neuromodulator for use by the neuromodulator in generating the electrical stimulation signals; and
distribute power signals to the neuromodulator; and using a control module having a microprocessor, a memory having at least one stored algorithm for generating neural stimulation patterns in response to the second electrical signals received from the aggregator module, and an on-board battery, and being configured to be carried on a person, to communicate via a transceiver with the aggregator module and to generate the third electrical signals used by the aggregator module;

further using the aggregator module, having an embedded processor and a housing, an internally mounted circuit board, and configured for implantation in a bodypart of the person, wherein the housing includes a surface having a recess configured to support the electrical connections component therein which is sealed via a separate overmold component affixed to the housing, such that the overmold component does not impede access to the internally mounted circuit board or the embedded processor, and the implantable electrical connections being configured to communicate the second and third electrical signals between the control module and the aggregator module, and the power signals to the neuromodulator; and further using the control module to communicate the neural stimulation patterns back to the aggregator module via the transceiver.

16. The method of claim 15, further comprising using the neuromodulator to receive electrical brain activity signals generated within the brain, and to transmit information corresponding to the electrical brain activity signals to the aggregator module as the second electrical signals.

* * * * *